US012797362B2

(12) United States Patent
Jang et al.

(10) Patent No.: US 12,797,362 B2
(45) Date of Patent: Nov. 17, 2026

(54) FORMULATION FOR ORAL ADMINISTRATION, COMPRISING 1-(5-(2,4-DIFLUOROPHENYL)-1-((3-FLUOROPHENYL)SULFONYL)-4-METHOXY-1H-PYRROL-3-YL)-N-METHYLMETHANAMINE

(71) Applicant: Daewoong Pharmaceutical Co., Ltd., Gyeonggi-do (KR)

(72) Inventors: Hye Jung Jang, Gyeonggi-do (KR); Do Hoon Kuk, Gyeonggi-do (KR); Gyoung Won Kim, Gyeonggi-do (KR); Gwan Young Kim, Gyeonggi-do (KR); Songyi Ha, Gyeonggi-do (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 509 days.

(21) Appl. No.: 18/267,939

(22) PCT Filed: Dec. 17, 2021

(86) PCT No.: PCT/KR2021/019265
§ 371 (c)(1),
(2) Date: Jun. 16, 2023

(87) PCT Pub. No.: WO2022/131844
PCT Pub. Date: Jun. 23, 2022

(65) Prior Publication Data

US 2025/0073205 A1 Mar. 6, 2025

(30) Foreign Application Priority Data

Dec. 18, 2020 (KR) ........................ 10-2020-0178281

(51) Int. Cl.
*A61K 31/40* (2006.01)
*A61K 9/00* (2006.01)
*A61K 9/20* (2006.01)
*A61K 9/28* (2006.01)

(52) U.S. Cl.
CPC ............ *A61K 31/40* (2013.01); *A61K 9/0053* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2095* (2013.01); *A61K 9/284* (2013.01); *A61K 9/2893* (2013.01)

(58) Field of Classification Search
CPC .. A61K 9/2018; A61K 9/2054; A61K 9/2095; A61K 31/40; A61K 9/0053; A61K 9/2013; A61K 9/2027
See application file for complete search history.

(56) References Cited

U.S. PATENT DOCUMENTS

| | | | | |
|---|---|---|---|---|
| 10,100,010 | B1 | 10/2018 | Lee et al. | |
| 2005/0267189 | A1 | 12/2005 | Gao et al. | |
| 2010/0041688 | A1 | 2/2010 | Park et al. | |
| 2011/0207826 | A1* | 8/2011 | Schwarz | A61K 47/38 514/263.34 |
| 2012/0148634 | A1 | 6/2012 | Dodd et al. | |
| 2014/0107107 | A1 | 4/2014 | Gautschi et al. | |
| 2017/0027871 | A1 | 2/2017 | Im et al. | |
| 2018/0153878 | A1 | 6/2018 | Park et al. | |
| 2019/0031609 | A1 | 1/2019 | Kim et al. | |
| 2021/0221770 | A1 | 7/2021 | Shin et al. | |

FOREIGN PATENT DOCUMENTS

| | | | | |
|---|---|---|---|---|
| JP | 2002-531403 | A | 9/2002 | |
| JP | 2010-513474 | A | 4/2010 | |
| JP | 2012-524722 | A | 10/2012 | |
| JP | 2015-531365 | A | 11/2015 | |
| JP | 2017-501126 | A | 1/2017 | |
| JP | 2018-058909 | A | 4/2018 | |
| JP | 2018-519279 | A | 7/2018 | |
| JP | 2019-509320 | A | 4/2019 | |
| KR | 2015-0067777 | A | 6/2015 | |
| KR | 10-1613245 | B1 | 4/2016 | |
| KR | 2016-0127646 | A | 11/2016 | |
| KR | 2017-0113040 | A | 10/2017 | |
| KR | 2018-0049510 | A | 5/2018 | |
| KR | 2018-0110826 | A | 10/2018 | |
| KR | 20200033178 | A | 3/2020 | |
| KR | 10-2126576 | B1 | 6/2020 | |
| TW | 201737908 | A | 11/2017 | |
| WO | WO-2017164576 | A1 * | 9/2017 | A61P 1/04 |

OTHER PUBLICATIONS

N. Patel et al. (International Journal of Pharmaceutics 110 (1994) 203-210. (Year: 1994).*
Search Report in International Application No. PCT/KR2021/019265 Apr. 1, 2022, 5 pages.
Benjamin Murugesu, "Milling", 24 pages, Pharmaceutical dosage forms: vol. 2, 2nd Edition, Ed.: H. A .Lieberman, L. Lachman, J. B. Schwartz (Chapter 3: Size Reduction), Jun. 3, 2008.
Office Action in JP Application No. 2023-536831 dated May 13, 2025, 11 pages.
Office Action in CN Application No. 202180085086.0 dated Sep. 20, 2025, 11 pages.
Office Action in TW Application No. 110147512 dated Jul. 22, 2025, 15 pages.

* cited by examiner

*Primary Examiner* — James H Alstrum-Acevedo
*Assistant Examiner* — Manahil Mirghani Ali Abdalhameed
(74) *Attorney, Agent, or Firm* — MARSHALL, GERSTEIN & BORUN LLP

(57) ABSTRACT

The present disclosure relates to a formulation for oral administration comprising 1-(5-(2,4-difluorophenyl)-1-((3-fluorophenyl)sulfonyl)-4-methoxy-1H-pyrrol-3-yl)-N-methylmethanamine exhibiting improved dissolution properties.

15 Claims, 3 Drawing Sheets

【FIG. 1】
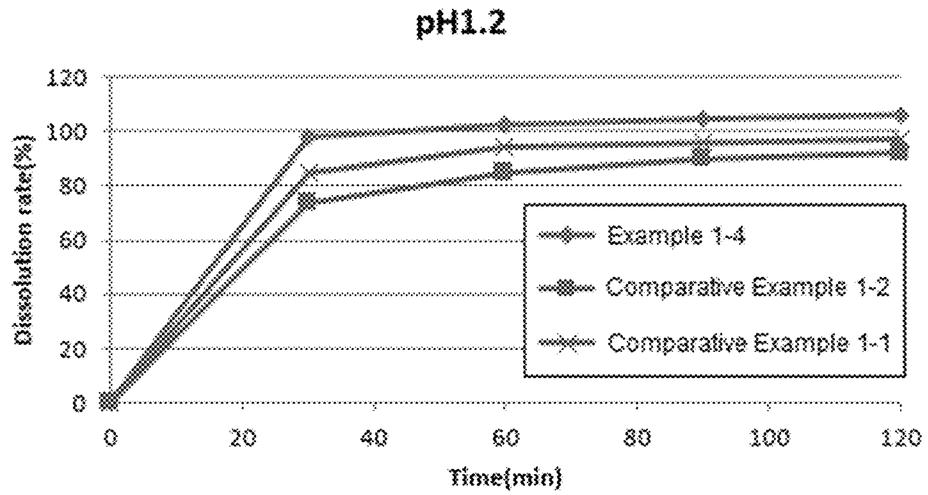
【FIG. 2】
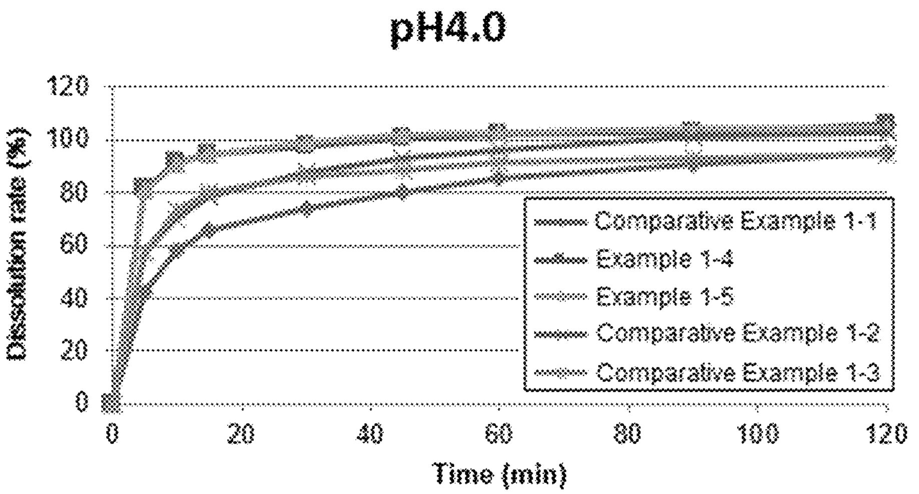

【FIG. 3】
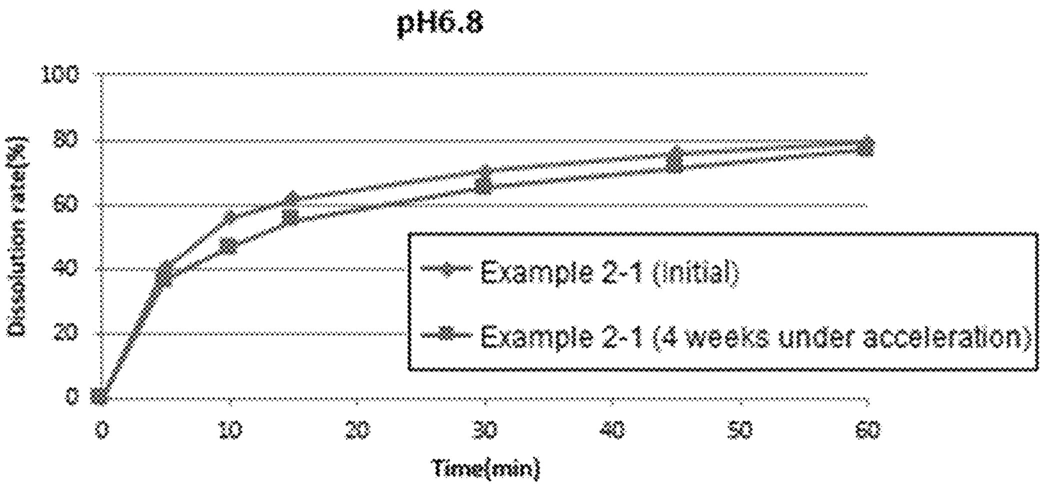
【FIG. 4】
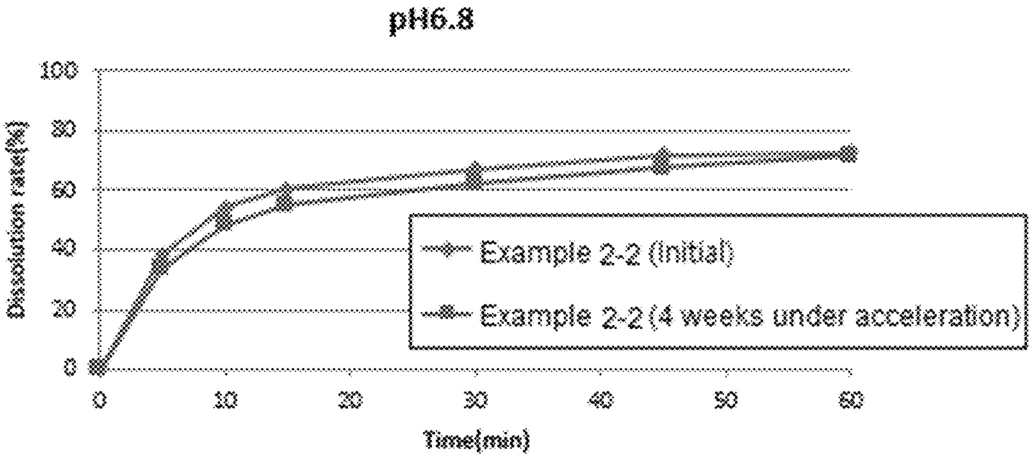

【FIG. 5】
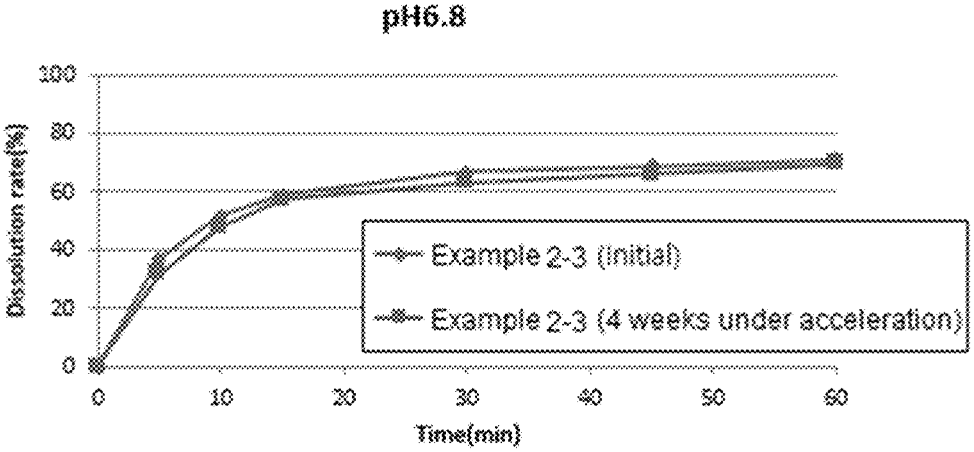
【FIG. 6】
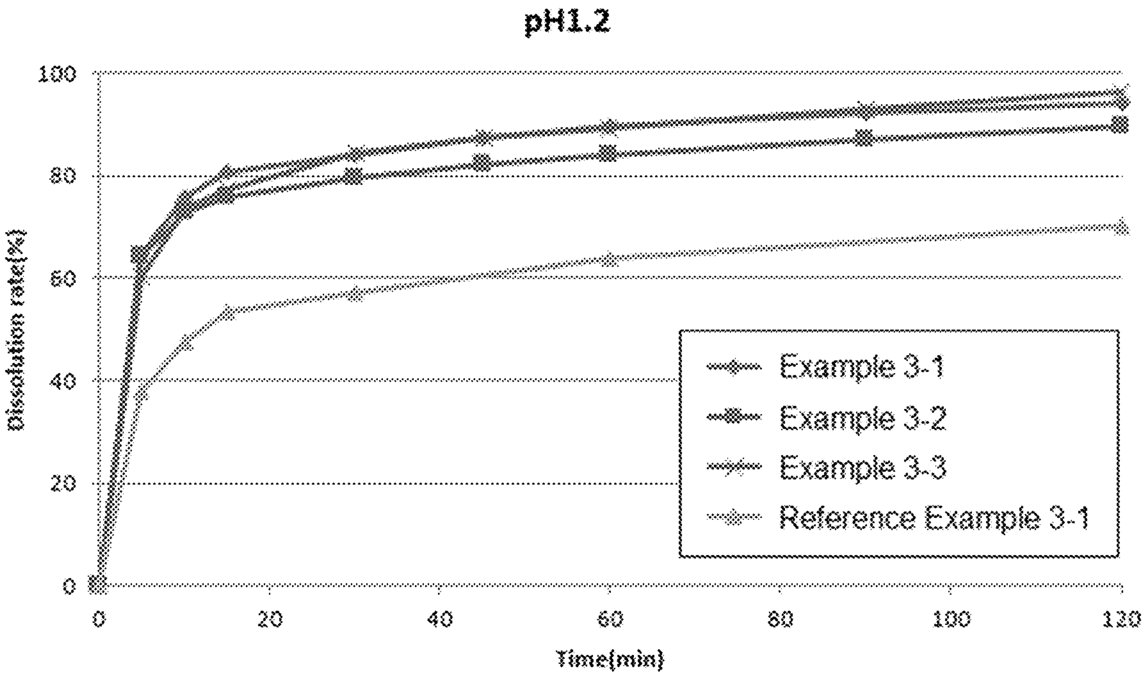

FORMULATION FOR ORAL ADMINISTRATION, COMPRISING 1-(5-(2,4-DIFLUOROPHENYL)-1-((3-FLUOROPHENYL)SULFONYL)-4-METHOXY-1H-PYRROL-3-YL)-N-METHYLMETHANAMINE

TECHNICAL FIELD

The present disclosure relates to a novel formulation for oral administration including 1-(5-(2,4-difluorophenyl)-1-((3-fluorophenyl) sulfonyl)-4-methoxy-1H-pyrrol-3-yl)-N-methylmethanamine.

BACKGROUND ART

It is known that even in a formulation containing the same active ingredient, pharmaceutically important properties such as solubility, dissolution properties, and bioavailability of the active ingredient may show differences depending on additional constituents contained in the formulation. Therefore, along with the development of new compounds, it is also very important to develop the constituents contained in the formulation capable of maximizing the pharmacological effects of the developed compound.

On the other hand, 1-(5-(2,4-difluorophenyl)-1-((3-fluorophenyl) sulfonyl)-4-methoxy-1H-pyrrol-3-yl)-N-methylmethanamine is a pharmaceutical active ingredient described in Korean Patent Registration No. 10-1613245, which has excellent anti-ulcer activity (i.e., proton pump inhibitory activity, etc.) and eradication activity against *H. pylori* (*Helicobacter pylori*) and inhibitory activity against GPCR, and thus is a substance useful for the prevention and treatment of gastrointestinal ulcers, gastritis, reflux esophagitis, or gastrointestinal damage due to *H. pylori.*

However, the compound has a problem that the water solubility is low and the dissolution rate decreases as the storage period elapses. By the way, in order to ensure that a pharmaceutical active ingredient exhibiting low water solubility usually has high dissolution properties, it is common to use an excessive amount of soluble additives, but there has been a problem that hypersensitivity may occur when a drug containing a large amount of such an additive is administered. Therefore, in order to develop an oral formulation in which a compound exhibiting low water solubility can have improved dissolution properties without adding a separate functional additive such as a soluble additive, it is necessary to study the combination of various ingredients in addition to pharmaceutically active ingredients.

Accordingly, the present inventors have attempted to variously formulate 1-(5-(2,4-difluorophenyl)-1-((3-fluorophenyl) sulfonyl)-4-methoxy-1H-pyrrol-3-yl)-N-methylmethanamine for improving its dissolution properties, and as a result, confirmed that in the case of a formulation for oral administration containing microcrystalline cellulose and lactose hydrate used as excipients in a specific weight ratio, the compound can exhibit excellent dissolution properties, and such excellent dissolution properties can be more effectively exhibited by adjusting the particle size to a specific size or less, thereby completing the present disclosure.

DETAILED DESCRIPTION OF THE INVENTION

Technical Problem

It is one object of the present disclosure to provide a formulation for oral administration comprising 1-(5-(2,4-difluorophenyl)-1-((3-fluorophenyl) sulfonyl)-4-methoxy-1H-pyrrol-3-yl)-N-methylmethanamine or a pharmaceutically acceptable salt thereof, that exhibits excellent dissolution properties, prevents decreases in dissolution rates and is excellent in storage stability.

Technical Solution

In order to achieve the above object, according to the present disclosure, there is provided a formulation for oral administration comprising: 1) a compound represented by the following Chemical Formula 1 or a pharmaceutically acceptable salt thereof; and 2) an excipient comprising lactose hydrate and microcrystalline cellulose, wherein the lactose hydrate and the microcrystalline cellulose are contained in a weight ratio of 1:1.5 to 1:90:

[Chemical Formula 1]

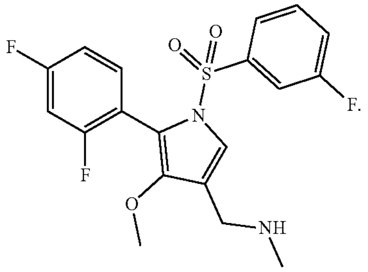

The chemical name of the compound represented by Chemical Formula 1 is 1-(5-(2,4-difluorophenyl)-1-((3-fluorophenyl) sulfonyl)-4-methoxy-1H-pyrrole-3-yl)-N-methylmethanamine, which is a pharmaceutically active ingredient having a molecular weight of 410.41, and is a substance described in Korean Patent Registration No. 10-1613245.

The compound represented by Chemical Formula 1 is an active ingredient exhibiting a pharmacological effect in the formulation for oral administration, which has excellent anti-ulcer activity (i.e., proton pump inhibitory activity, etc.) and eradication activity against *H. pylori* and inhibitory activity against GPCR, and thus is a substance useful for the prevention and treatment of gastrointestinal ulcers, gastritis, reflux esophagitis, or gastrointestinal damage due to *Helicobacter pylori.*

In addition to the compound represented by Chemical Formula 1, a pharmaceutically acceptable salt thereof can be used as the active ingredient exhibiting the pharmacological effect of the formulation for oral administration of the present disclosure. As such a salt, a salt commonly used in the art, such as an acid addition salt formed with a pharmaceutically acceptable free acid, can be used, without limitation. The term “pharmaceutically acceptable salt” as used herein refers to any organic or inorganic addition salt of the compound of Chemical Formula 1 whose concentration exhibits relatively non-toxic and harmless effective actions to a patient, and whose side effects do not decrease the beneficial efficacy of the above compound.

The pharmaceutically acceptable salt of the compound represented by Chemical Formula 1 can be obtained by a conventional method using an inorganic acid or an organic acid. For example, the pharmaceutically acceptable salt can be prepared by dissolving the compound represented by Chemical Formula 1 in a water-miscible organic solvent such as acetone, methanol, ethanol or acetonitrile, adding an organic acid or an inorganic acid thereto, filtering and drying the precipitated crystals. Alternatively, it may be prepared by subjecting a solvent or an excessive amount of the acid-added reaction mixture to reduced pressure and then drying the residue, or may be prepared by adding a different organic solvent and then filtering the precipitated salt. At this time, the preferred salts may include salts derived from hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid or toluenesulfonic acid, and the like. More preferably, the pharmaceutically acceptable salt of the compound represented by Chemical Formula 1 may be hydrochloride or fumarate.

As described above, the compound represented by Chemical Formula 1 or a pharmaceutically acceptable salt thereof has a problem that the water solubility is low, the dissolution rate decreases as the storage period elapses, and thus the bioavailability and the expression of the medicinal efficacy may become unstable. However, when specific excipients are used in combination at a specific weight ratio, the dissolution phenomenon of the compound represented by Chemical Formula 1 or a pharmaceutically acceptable salt thereof is remarkably improved, and it can be used as a formulation in which storage stability is ensured. Specifically, the formulation for oral administration comprising the compound represented by Chemical Formula 1 or a pharmaceutically acceptable salt thereof and two types of excipients, lactose hydrate (lactose monohydrate) and microcrystalline cellulose (MCC) in a specific weight ratio can exhibit a high initial dissolution rate and, at the same time, exhibit excellent dissolution properties even after the lapse of time. Accordingly, the formulation for oral administration exhibits stable dissolution in the environment in the in vivo stomach, and can ensure the continuous expression of medicinal efficacy.

This is demonstrated by Experimental Examples described later. Specifically, it can be seen that the formulation including the compound represented by Chemical Formula 1 or a pharmaceutically acceptable salt thereof exhibits a stable dissolution rate under all conditions of pH 1.2, pH 4.0 and pH 6.8, based on the dissolution test in the general test method as set forth in the Korean Pharmacopoeia. Therefore, since the formulation will exhibit a stable dissolution rate in vivo under the conditions showing such pHs, it is expected that the bioavailability of the active ingredient in the formulation will also be improved in both the stomach and small intestine environment in vivo.

At this time, the term 'excipient' as used herein is a pharmaceutically acceptable ingredient used to make a product form favorable to take the active ingredient exhibiting the pharmacological effect of the formulation for oral administration of the present disclosure. As commonly used excipients, sucrose, D-mannitol, starch, corn starch, light anhydrous silicic acid, and the like are known in addition to microcrystalline cellulose and lactose hydrate. However, among various known excipients, it is suitable to use a combination of two types of microcrystalline cellulose and lactose hydrate in a specific weight ratio to improve the dissolution properties of the active ingredient. This can be confirmed in Examples described later.

Preferably, in the formulation for oral administration, lactose hydrate and microcrystalline cellulose are used in combination without addition of other excipients as excipients. In other words, the excipient comprises lactose hydrate and microcrystalline cellulose, and the lactose hydrate and the microcrystalline cellulose are contained in a weight ratio of 1:1.5 to 1:90. When the lactose hydrate and the microcrystalline cellulose are contained in a weight ratio of less than 1:1.5, or when only one type of the above excipients is used, it is difficult to ensure a producible and desirable level of harness of the tablet, or there is a problem that the active ingredient is not completely dissolved out even after the lapse of time. In addition, when the lactose hydrate and the microcrystalline cellulose are contained in a weight ratio of more than 1:90, due to the properties of microcrystalline cellulose that is not easily soluble in water, there arises a problem that the initial dissolution rate of the active ingredient is lowered.

Specifically, the formulation for oral administration containing the lactose hydrate and the microcrystalline cellulose in a weight ratio of 1:1.5 to 1:90 in addition to the active ingredient has an initial dissolution rate (dissolution rate after 5 minutes) of 60% or more, and reach a final dissolution rate (dissolution rate after 120 minutes) of 100%, when tested according to the dissolution test II (paddle method) in the general test method as set forth in the Korean Pharmacopoeia 11th edition. At this time, when the initial dissolution rate (dissolution rate after 5 minutes) of the active ingredient of the formulation for oral administration is less than 60%, there may be a problem that it is difficult to show immediate and effective medicinal efficacies, and when the final dissolution rate (dissolution rate after 120 minutes) does not reach 100%, it is difficult to sufficiently exhibit the intended medicinal effect, and thus is not suitable for use as a formulation.

More preferably, in the formulation for oral administration, the lactose hydrate and the microcrystalline cellulose are contained in a weight ratio of 1:3.4 to 1:5.0. Specifically, in the formulation for oral administration, the lactose hydrate and the microcrystalline cellulose are contained in the weight ratio of 1:1.5 or more, 1:2.0 or more, 1:2.5 or more, 1:3.0 or more, 1:3.2 or more, or 1:3.4 or more, and 1:80 or less, 1:70 or less, 1:60 or less, 1:50 or less, 1:40 or less, 1:30 or less, 1:25 or less, 1:20 or less, 1:10 or less, or 1:5.0 or less.

Preferably, the excipient may be contained in the formulation for oral administration in an amount of 100 to 1400 parts by weight based on 100 parts by weight of the compound represented by Chemical Formula 1 or a pharmaceutically acceptable salt thereof. When the content of the excipient is less than 100 parts by weight, it is difficult to secure a producible and desirable level of granules and tablets. When the content of the excipient is more than 1400 parts by weight, there is a problem that the total weight of the formulation is unnecessarily increased, and thus the patient's convenience of taking the drug is deteriorated or the dissolution is delayed. Preferably, the excipient is contained in an amount of 200 to 650 parts by weight based on 100 parts by weight of the compound represented by Chemical Formula 1 or a pharmaceutically acceptable salt thereof. More specifically, the excipient can be contained in an amount of 200 parts by weight or more, 210 parts by weight or more, 220 parts by weight or more, 230 parts by weight or more, or 240 parts by weight or more, and 650 parts by weight or less, 550 parts by weight or less, 500 parts by weight or less, 450 parts by weight or less, 400 parts by weight or less, 350 parts by weight or less, or 300 parts by weight or less, based on 100 parts by weight of the compound represented by Chemical Formula 1 or a pharmaceutically acceptable salt thereof.

Preferably, the lactose hydrate is contained in the formulation for oral administration in an amount of 1 to 350 parts by weight based on 100 parts by weight of the compound represented by Chemical Formula 1 or a pharmaceutically acceptable salt thereof. When the lactose hydrate is contained in an amount of less than 1 part by weight, it is difficult to show adequate medicinal efficacy due to the low dissolution rate at the beginning. When the lactose hydrate is contained in an amount of more than 350 parts by weight, there is a problem that the total weight of the formulation is unnecessarily increased or the dissolution is delayed.

More preferably, the lactose hydrate is contained in the formulation for oral administration in an amount of 2.55 to 150 parts by weight based on 100 parts by weight of the compound represented by Chemical Formula 1 or a pharmaceutically acceptable salt thereof. Specifically, in the formulation for oral administration, the lactose hydrate is contained in an amount of 2.55 or more, 5 or more, 10 parts by weight or more, 20 parts by weight or more, 30 parts by weight or more, 40 parts by weight or more, or 50 parts by weight or more, and 150 parts by weight or less, 130 parts by weight or less, 120 parts by weight or less, or 110 parts by weight or less based on 100 parts by weight of the compound represented by Chemical Formula 1 or a pharmaceutically acceptable salt thereof.

Preferably, the microcrystalline cellulose is contained in the formulation for oral administration in an amount of 50 to 1100 parts by weight based on 100 parts by weight of the compound represented by Chemical Formula 1 or a pharmaceutically acceptable salt thereof. When the microcrystalline cellulose is contained in an amount of less than 50 parts by weight, it is difficult to exhibit adequate and intended medicinal effect, and when the microcrystalline cellulose is contained in an amount of more than 1100 parts by weight, there is a problem that the total weight of the formulation is unnecessarily increased or the dissolution is delayed.

More preferably, the microcrystalline cellulose is contained in an amount of 150 to 500 parts by weight based on 100 parts by weight of the compound represented by Chemical Formula 1 or a pharmaceutically acceptable salt thereof. Specifically, in the formulation for oral administration, the microcrystalline cellulose is contained in an amount of 150 parts by weight or more, 160 parts by weight or more, 180 parts by weight or more, 190 parts by weight or more, and 540 parts by weight or less, 530 parts by weight or less, 520 parts by weight or less, 500 parts by weight or less, 400 parts by weight or less, 300 parts by weight or less, or 250 parts by weight or less, based on 100 parts by weight of the compound represented by Chemical Formula 1 or a pharmaceutically acceptable salt thereof.

On the other hand, the formulation for oral administration may further include a disintegrant. As used herein, the term 'disintegrant' means a pharmaceutically acceptable ingredient added to promote the disintegration of the active ingredient by swelling. As the disintegrant, croscarmellose sodium, granulated mannitol powder, crospovidone, carboxymethyl cellulose calcium, sodium starch glycolate, starch or the like can be used. At this time, from the viewpoint that the storage stability can be further improved without occurring a phenomenon where the dissolution rates and contents are decreased under conditions similar to the environment in the gastrointestinal tract of the living body, it is preferable to use at least one selected from the group consisting of croscarmellose sodium, carboxymethyl cellulose calcium and sodium starch glycolate as the disintegrant.

Further, preferably, the disintegrant is contained in the formulation for oral administration in an amount of 3.5 to 80 parts by weight based on 100 parts by weight of the compound represented by Chemical Formula 1 or a pharmaceutically acceptable salt thereof. When the disintegrant is contained in an amount of less than 3.5 parts by weight, the disintegration of the active ingredient is excessively delayed and the desired bioavailability could not be obtained. When the disintegrant is contained in an amount of more than 80 parts by weight, the swelling phenomenon due to the wettability of the disintegrant is caused, making it impossible to secure the properties and quality of the formulation. More preferably, the disintegrant is contained in an amount of 5 parts by weight or more, 10 parts by weight or more, 12 parts by weight or more, or 14 parts by weight or more, and 70 parts by weight or less, 60 parts by weight or less, 50 parts by weight or less, 40 parts by weight or less, or 35 parts by weight or less, based on 100 parts by weight of the compound represented by Chemical Formula 1 or a pharmaceutically acceptable salt thereof.

Moreover, the formulation for oral administration may further include at least one additive selected from the group consisting of a binder, a lubricant, a colorant, and a coating agent.

The binder is added in order to maintain the formulation form. As the binder, hydroxypropyl cellulose, hydroxypropyl methyl cellulose, polyvinylpyrrolidone, copovidone, starch, microcrystalline cellulose, colloidal silicon dioxide, mannitol, lactose, polyethylene glycol and mixtures thereof, but the present disclosure is not limited thereto.

The lubricant is added in order to increase the filling properties of the pharmaceutical formulation and facilitate compression. As the lubricant, at least one selected among stearic acid, magnesium stearate, calcium stearate, sodium benzoate, sodium stearyl fumarate, glyceryl monoolate, glyceryl monostearate, glyceryl behenate, glyceryl palmitostearate, zinc stearate and paraffins, but the present disclosure is not limited thereto. Preferably, magnesium stearate is used as the lubricant from the viewpoint of the ease of the manufacturing process.

Further, titanium oxide, yellow iron oxide, red iron oxide, black iron oxide, titanium dioxide, talc, and the like can be used as the colorant, but the present disclosure is not limited thereto. Preferably, from an aesthetic point of view, yellow iron oxide is used as the colorant.

Further, as the coating agent, Opadry® including Opadry White, Opadry Pink, Opadry Green, Opadry Orange, Opadry Blue, Opadry Yellow, Opadry Brown, and the like can be used.

Preferably, the formulation for oral administration further includes at least one compound selected from the group consisting of croscarmellose sodium, carboxymethyl cellulose calcium and sodium starch glycolate; and magnesium stearate.

More preferably, the formulation for oral administration further includes at least one compound selected from the group consisting of croscarmellose sodium, carboxymethyl cellulose calcium and sodium starch glycolate; magnesium stearate; and yellow iron oxide.

More specifically, the formulation for oral administration may include 100 parts by weight of the compound represented by Chemical Formula 1 or a pharmaceutically acceptable salt thereof; 200 to 650 parts by weight of an excipient comprising lactose hydrate and microcrystalline cellulose; 5 to 35 parts by weight of at least one disintegrant selected from the group consisting of croscarmellose sodium, carboxymethylcellulose calcium and sodium starch glycolate; 5 to 20 parts by weight of magnesium stearate lubricant; and 0.01 to 1 part by weight of a yellow iron oxide colorant.

On the other hand, the compound represented by Chemical Formula 1 or a pharmaceutically acceptable salt thereof is contained in the formulation for oral administration in an amount of 5 to 50% by weight based on the total weight of the formulation for oral administration. When the active ingredient is contained in the formulation for oral administration within the above-mentioned range, the pharmacological activity due to the active ingredient can be effectively exhibited.

More preferably, the compound represented by Chemical Formula 1 or a pharmaceutically acceptable salt thereof is contained in an amount of 10 to 30% by weight based on the total weight of the formulation for oral administration. Specifically, the compound represented by Chemical Formula 1 or a pharmaceutically acceptable salt thereof may be contained in an amount of 10% by weight or more, 10.5% by weight or more, 11% by weight or more, 11.5% by weight or more, 12% by weight or more, or 12.5% by weight or more, and 30% by weight or less, 29.5% by weight or less, 29% by weight or less, 28.5% by weight or less, 28% by weight or less, 27.5% by weight or less, or 27% by weight or less, based on the total weight of the formulation for oral administration.

On the other hand, the dissolution profile of the compound represented by Chemical Formula 1 may vary depending on the particle size distribution of the compound. In particular, since the compound represented by Chemical Formula 1 is preferably formulated into an immediate release type due to the characteristics of the drug, in order to achieve this, it is necessary to adjust the particle size distribution of the compound represented by Chemical Formula 1.

Preferably, the particle size ($D_{50}$) of the compound represented by Chemical Formula 1 or a pharmaceutically acceptable salt thereof is 100 μm or less. When the particle size ($D_{50}$) of the compound represented by Chemical Formula 1 or a pharmaceutically acceptable salt thereof exceeds 100 μm, the initial dissolution rate is not very good and the final dissolution rate is also not good, and thus it may be difficult to formulate into an immediate release type. Specifically, the particle size ($D_{50}$) of the compound represented by Chemical Formula 1 or a pharmaceutically acceptable salt thereof may be 90 μm or less, 85 μm or less, 80 μm or less, 75 μm or less, 70 μm or less, or 65 μm or less.

More preferably, the particle size ($D_{50}$) of the compound represented by Chemical Formula 1 or a pharmaceutically acceptable salt thereof is 10 μm to 65 μm. Specifically, the particle size ($D_{50}$) of the compound represented by Chemical Formula 1 or a pharmaceutically acceptable salt thereof may be 10 μm or more, 11 μm or more, 12 μm or more, 13 μm or more, 14 μm or more, or 15 μm or more, and 65 μm or less, 60 μm or less, 50 μm or less, 40 μm or less, 30 μm or less, 25 μm or less, 20 μm or less, 19 μm or less, or 18 μm or less.

When the compound represented by Chemical Formula 1 or a pharmaceutically acceptable salt thereof has a particle size within the above-mentioned range, the dissolution rate of the compound is further improved and the rate of absorption in the body is increased, so that the pharmacological activity in the human body can be increased. Furthermore, the compound having a particle size in the above-mentioned range can be formulated into an immediate release type.

As used herein, the "particle size ($D_x$)=Y (where X and Y are positive numbers)" means that, when a particle size distribution of a particle obtained by measuring a diameter of a particle is represented as a cumulative curve, a point where particle sizes accumulate in ascending order and the result reaches X % (where % is calculated based on a number, a volume, or a weight) has a particle diameter of Y. Therefore, particle size ($D_{10}$) represents the diameter of particles at a cumulative 10% point in the cumulative particle size distribution curve, particle size ($D_{50}$) represents the diameter of particles at a cumulative 50% point in the cumulative particle size distribution curve, and particle size ($D_{90}$) represents the diameter of particles at a cumulative 90% point in the cumulative particle size distribution curve. Further, the particle size ($D_x$) may vary depending on whether it represents a percentage of the total accumulated particles based on any of a number, a volume, and a weight. The method of measuring the particle size distribution and a type of % related thereto are known in the related art.

In this time, the particle size ($D_x$) of the compound represented by Chemical Formula 1 or a pharmaceutically acceptable salt thereof is preferably measured by a laser diffraction method in which the particle size is recorded as the diameter of a volume equivalent sphere. In other words, when the particle size distribution is measured by the laser diffraction method, the value of X in the particle size ($D_x$) represents the percentage calculated by the volume average. Thus, in the laser diffraction method, a volume average particle size is provided to correspond to a volume of a particle, which corresponds to a weight average particle size when a density is constant.

The measurement of the volume average particle size distribution of the compound represented by Chemical Formula 1 or a pharmaceutically acceptable salt thereof by the laser diffraction method can be performed using a commercially available device using a laser diffraction and scattering method based on a Mie theory. For example, the particle size distribution of the compound represented by Chemical Formula 1 or a pharmaceutically acceptable salt thereof can be measured using a Mastersizer laser diffraction device of Malvern Instruments. This device is used to obtain a particle diameter distribution such that, when a helium-neon laser beam or a blue light emitting diode emits light toward particles, scattering is caused, a light scattering pattern is shown in a detector, and this light scattering pattern is analyzed according to the Mie theory, which is advantageous in that any of dry and wet methods can be used as the measurement method.

Further, the compound represented by Chemical Formula 1 or a pharmaceutically acceptable salt thereof satisfying the desired particle size distribution can be obtained by performing pulverization and then classification according to the particle size using a micronizing device. Specifically, the pulverization can be performed using a general mill such as a Z-mill, a hammer mill, a ball mill, a fluid energy mill or the like. Then, the particle size of the pulverized product can be subdivided by a sieve method using a sieve or a size classification method such as air current classification. More specifically, a method of regulating a desired particle size is well-known in the related art [Pharmaceutical dosage forms: Volume 2, 2nd Edition, Ed.: H. A. Lieberman, L. Lachman, J. B. Schwartz (Chapter 3: SIZE REDUCTION)].

On the other hand, the dosage of the compound represented by Chemical Formula 1 or a pharmaceutically acceptable salt thereof, which is an active ingredient in the formulation, is appropriately determined depending on the individual case, in consideration of the symptoms, a patient's age and gender, and the like. However, in the case of oral administration, the dosage for adults is usually 0.01 mg/kg or more per day and 100 mg/kg or less per day, and this can be administered at one time.

Further, the formulation may have a total weight of 80 mg to 650 mg. Preferably, the formulation has a total weight of 80 mg to 350 mg. Specifically, the formulation has a total weight of 80 mg or more, or 90 mg or more, and 350 mg or less, 320 mg or less, 250 mg or less, 200 mg or less, or 180 mg or less.

Preferably, when the compound represented by Chemical Formula 1 or a pharmaceutically acceptable salt thereof, which is the active ingredient in the formulation, is used for the main purpose of preventing and treating gastrointestinal ulcers, gastritis, reflux esophagitis, or gastrointestinal damage due to *H. pylori*, the active ingredient is contained in an amount of 10 mg to 80 mg per one formulation. In one example, the active ingredient may be contained in an amount of 10 mg, 20 mg, 40 mg, or 80 mg per one formulation.

Further, the formulation for oral administration is prepared as a preparation such as a tablet, a capsule, a granule, a powder, and the like in consideration of use, function, administration route, and the like. Preferably, the formulation for oral administration is a tablet.

In addition, the formulation for oral administration can be prepared by including the steps of: mixing lactose hydrate, microcrystalline cellulose, and optionally, a lubricant with the compound represented by Chemical Formula 1 or a pharmaceutically acceptable salt thereof, and then subjecting to compression and pulverization granulation to prepare a dry granule; and mixing the dry granulate with a disintegrant and, if necessary, other additives and compressing the mixture into a tablet.

However, the present disclosure is not limited to such preparation method, and the preparation of the formulation for oral administration can be modified according to methods known in the art.

Advantageous Effects

As described above, a formulation for oral administration comprising 1-(5-(2,4-difluorophenyl)-1-((3-fluorophenyl) sulfonyl)-4-methoxy-1H-pyrrol-3-yl)-N-methylmethanamine or a pharmaceutically acceptable salt thereof according to the present disclosure include lactose hydrate and microcrystalline cellulose as excipients that satisfy certain weight ratios, and thus can be used as a formulation for oral administration that can exhibit excellent dissolution properties and is useful for the prevention and treatment of gastrointestinal ulcers, gastritis, reflux esophagitis, or gastrointestinal damage due to *H. pylori.*

BRIEF DESCRIPTION OF THE DRAWING

FIG. 1 is a graph for comparing dissolution rates of the tablets prepared in Comparative Example 1-1, Comparative Example 1-2, and Example 1-4 in a pH 1.2 test solution;

FIG. 2 is a graph for comparing the dissolution rates of the tablets prepared in Comparative Examples 1-1 to 1-3, Examples 1-4 and Example 1-5 in a pH 4.0 test solution;

FIG. 3 is a graph for comparing the dissolution rate conditions of the tablets prepared in Example 2-1 in a pH 6.8 test solution under the initial condition and accelerated condition;

FIG. 4 is a graph for comparing the dissolution rate conditions of the tablets prepared in Example 2-2 in a pH 6.8 test solution under the initial condition and accelerated condition;

FIG. 5 is a graph for comparing the dissolution rate conditions of the tablets prepared in Example 2-3 in a pH 6.8 test solution under the initial condition and accelerated condition; and FIG. 6 is a graph for comparing the dissolution rates of the tablets prepared in Examples 3-1 to 3-3 and Reference Example 3-1 in a pH 1.2 test solution.

DETAILED DESCRIPTION OF THE EMBODIMENTS

Hereinafter, preferred examples are presented to help the understanding of the present disclosure, but the following examples are for illustrative purposes only, and are not intended to limit the scope of the present disclosure.

Example 1-1

1-(5-(2,4-difluorophenyl)-1-((3-fluorophenyl) sulfonyl)-4-methoxy-1H-pyrrol-3-yl)-N-methylmethanamine hydrochloride (hereinafter, abbreviated as API (active pharmaceutical ingredients; active ingredient)), which is the compound represented by Chemical Formula 1 as the main component was prepared by the method described in Examples of Korean Patent Registration No. 10-2126576, which was then mixed with microcrystalline cellulose, lactose hydrate and magnesium stearate. Then, the mixture was compressed by a roller compactor to prepare a plate-like compressed product, which was pulverized and granulated by an oscillator to prepare a dry granule. Croscarmellose sodium, yellow iron oxide and magnesium stearate were added to the prepared granule and mixed, and the resulting mixture was compressed to prepare a tablet. In this case, the contents of the components contained in the tablet of Example 1-1 are as shown in Table 1 below.

Examples 1-2 to 1-16 and Comparative Examples 1-1 to 1-3

A tablet was prepared in the same manner as in Example 1-1, except that in Example 1-1, only the ratio of microcrystalline cellulose and lactose hydrate used as excipients was used differently as shown in Tables 1 to 3 below.

TABLE 1

| Category | Component | (Amount used, part by weight) Comparative Example 1-1 | Example 1-1 | Example 1-2 | Example 1-3 | Example 1-4 | Example 1-5 | Example 1-6 |
|---|---|---|---|---|---|---|---|---|
| Main component | API | 100 | 100 | 100 | 100 | 100 | 100 | 100 |
| Excipient | Microcrystalline cellulose | 149.80 | 162.30 | 174.80 | 187.30 | 199.80 | 499.60 | 212.30 |
| | Lactose hydrate | 102.50 | 90.00 | 77.50 | 65.00 | 52.50 | 105.00 | 40.00 |

TABLE 1-continued

| Category | Component | Comparative Example 1-1 | Example 1-1 | Example 1-2 | Example 1-3 | Example 1-4 | Example 1-5 | Example 1-6 |
|---|---|---|---|---|---|---|---|---|
| | | (Amount used, part by weight) | | | | | | |
| Disintegrant | Croscarmellose sodium | 15 | 15 | 15 | 15 | 15 | 30 | 15 |
| Lubricant | Magnesium stearate | 7.5 | 7.5 | 7.5 | 7.5 | 7.5 | 15 | 7.5 |
| Colorant | Yellow iron oxide | 0.2 | 0.2 | 0.2 | 0.2 | 0.2 | 0.4 | 0.2 |
| Total amount | | 375 | 375 | 375 | 375 | 375 | 750 | 375 |
| Weight ratio of microcrystalline cellulose to lactose hydrate | | 1.46 | 1.80 | 2.26 | 2.88 | 3.81 | 4.76 | 5.31 |
| Main component content (wt. %) | | 26.67 | 26.67 | 26.67 | 26.67 | 26.67 | 13.33 | 26.67 |

TABLE 2

| Category | Component | Example 1-7 | Example 1-8 | Example 1-9 | Example 1-10 | Example 1-11 | Example 1-12 | Example 1-13 |
|---|---|---|---|---|---|---|---|---|
| | | (Amount used, part by weight) | | | | | | |
| Main component | API | 100 | 100 | 100 | 100 | 100 | 100 | 100 |
| Excipient | Microcrystalline cellulose | 224.80 | 237.30 | 239.80 | 242.30 | 244.80 | 246.05 | 247.30 |
| | Lactose hydrate | 27.50 | 15.00 | 12.50 | 10.00 | 7.50 | 6.25 | 5.00 |
| Disintegrant | Croscarmellose sodium | 15 | 15 | 15 | 15 | 15 | 15 | 15 |
| Lubricant | Magnesium stearate | 7.5 | 7.5 | 7.5 | 7.5 | 7.5 | 7.5 | 7.5 |
| Colorant | Yellow iron oxide | 0.2 | 0.2 | 0.2 | 0.2 | 0.2 | 0.2 | 0.2 |
| Total amount | | 375 | 375 | 375 | 375 | 375 | 375 | 375 |
| Weight ratio of microcrystalline cellulose to lactose hydrate | | 8.17 | 15.82 | 19.18 | 24.23 | 32.64 | 39.37 | 49.46 |
| Main component content (wt. %) | | 26.67 | 26.67 | 26.67 | 26.67 | 26.67 | 26.67 | 26.67 |

TABLE 3

| Category | Component | Example 1-14 | Example 1-15 | Example 1-16 | Comparative Example 1-2 | Comparative Example 1-3 |
|---|---|---|---|---|---|---|
| | | (Amount used, part by weight) | | | | |
| Main component | API | 100 | 100 | 100 | 100 | 100 |
| Excipient | Microcrystalline cellulose | 247.93 | 248.55 | 249.18 | 249.80 | 252.30 |
| | Lactose hydrate | 4.38 | 3.75 | 3.13 | 2.50 | — |
| Disintegrant | Croscarmellose sodium | 15 | 15 | 15 | 15 | 15 |
| Lubricant | Magnesium stearate | 7.5 | 7.5 | 7.5 | 7.5 | 7.5 |
| Colorant | Yellow iron oxide | 0.2 | 0.2 | 0.2 | 0.2 | 0.2 |
| Total amount | | 375 | 375 | 375 | 375 | 375 |
| Weight ratio of microcrystalline cellulose to lactose hydrate | | 56.67 | 66.28 | 79.74 | 99.92 | — |
| Main component content (wt. %) | | 26.67 | 26.67 | 26.67 | 26.67 | 26.67 |

Experimental Example 1: Dissolution Evaluation Test

The tablets prepared in Examples 1-1 to 1-16 and Comparative Examples 1-1 to 1-3 were subjected to an in vitro dissolution test and HPLC analysis with a pH 1.2 test solution and a pH 4.0 test solution, and the dissolution rate (%) was measured. The results of dissolution rate measurement in the pH 1.2 test solution are shown in Table 4 and FIG. 1, and the results of dissolution rate measurement in the pH 4.0 test solution are shown in Table 5 and FIG. 2, respectively. At this time, the conditions of the dissolution test are as follows.

1) Basis for dissolution test: dissolution test of the general test method as set forth in the Korean Pharmacopoeia 11th edition
2) Dissolution test: dissolution test II, Paddle method
3) Dissolution test solution: 900 mL of pH 1.2 test solution, 900 mL of pH 4.0 test solution
4) Temperature condition: maintained at 37.2° C.±0.5° C.
5) Analysis method: HPLC method Detector: ultraviolet absorbance spectrometer (measurement wavelength: 254 nm)

Column: C8 5 um/4.6×250 mm column

Mobile phase: hydrogen phosphate buffer: methanol pH 1.2 test solution: a first solution of the dissolution test according to the Korean Pharmacopoeia, which is a buffer solution prepared using hydrochloric acid and sodium chloride with a hydrochloric acid concentration of 0.1 mol/L pH 4.0 test solution: 0.05 mol/L sodium acetate buffer

TABLE 4

| Time (min) | 30 | 60 | 90 | 120 |
|---|---|---|---|---|
| Comparative Example 1-1 | 84.9 | 94.4 | 95.5 | 96.9 |
| Comparative Example 1-2 | 73.4 | 84.4 | 89.6 | 92.4 |
| Example 1-4 | 97.6 | 102.1 | 104.3 | 105.7 |

TABLE 5

| Time (min) | 5 | 10 | 15 | 30 | 45 | 60 | 90 | 120 |
|---|---|---|---|---|---|---|---|---|
| Comparative Example 1-1 | 42.4 | 58.1 | 65.4 | 74.2 | 80.3 | 85.0 | 90.8 | 95.5 |
| Example 1-1 | 75.1 | 89.2 | 91.9 | 95.9 | 98.3 | 99.7 | 102.9 | 102.9 |
| Example 1-2 | 79.9 | 84.2 | 88.0 | 93.0 | 95.4 | 98.4 | 101.1 | 102.3 |
| Example 1-3 | 75.5 | 86.5 | 90.5 | 93.9 | 96.9 | 99.6 | 101.8 | 103.2 |
| Example 1-4 | 81.9 | 91.7 | 94.2 | 97.3 | 100.6 | 101.7 | 103.0 | 106.0 |
| Example 1-5 | 80.8 | 90.5 | 94.2 | 99.3 | 101.7 | 103.1 | 104.2 | 104.5 |
| Example 1-6 | 79.8 | 91.9 | 96.4 | 99.5 | 102.0 | 102.3 | 103.2 | 103.7 |
| Example 1-7 | 78.1 | 92.5 | 96.8 | 100.1 | 102.2 | 103.7 | 104.8 | 105.7 |
| Example 1-8 | 79.8 | 91.6 | 96.0 | 99.9 | 101.2 | 102.4 | 103.0 | 104.3 |
| Example 1-9 | 78.5 | 93.4 | 98.6 | 102.7 | 103.3 | 104.8 | 105.6 | 106.8 |
| Example 1-10 | 79.3 | 92.8 | 97.0 | 101.4 | 102.1 | 104.4 | 104.5 | 106.4 |
| Example 1-11 | 78.5 | 91.7 | 96.7 | 100.1 | 101.7 | 102.7 | 102.6 | 103.6 |
| Example 1-12 | 78.0 | 88.0 | 93.1 | 98.1 | 100.3 | 101.4 | 102.6 | 103.6 |
| Example 1-13 | 74.3 | 86.9 | 92.9 | 97.6 | 99.3 | 101.0 | 102.9 | 103.3 |
| Example 1-14 | 74.2 | 86.7 | 92.1 | 97.2 | 101.5 | 101.0 | 103.7 | 104.2 |
| Example 1-15 | 73.7 | 87.6 | 93.1 | 98.4 | 100.4 | 101.3 | 102.5 | 103.9 |
| Example 1-16 | 73.1 | 88.3 | 92.1 | 95.4 | 97.9 | 99.7 | 100.8 | 101.1 |
| Comparative Example 1-2 | 57.6 | 70.0 | 78.3 | 87.5 | 93.1 | 96.0 | 101.0 | 102.9 |
| Comparative Example 1-3 | 57.3 | 73.6 | 79.9 | 86.3 | 88.6 | 91.5 | 92.8 | 94.2 |

Referring to Table 4 and FIG. 1, it can be confirmed that in the tablet of Examples 1-4, the final dissolution rate (dissolution rate at 120 minutes after the start of dissolution) reaches 100% under pH 1.2 conditions, whereas the tablet of Comparative Example 1-1, in which the weight ratio of the lactose hydrate and microcrystalline cellulose is less than 1:1.5 and the tablet of Comparative Example 1-2, in which the weight ratio of the lactose hydrate and microcrystalline cellulose is greater than 1:90, the main component is not completely dissolved out even after the lapse of 120 minutes, which is the final dissolution time.

In addition, referring to Table 5 and FIG. 2, it can be confirmed that in the tablets of Examples, the initial dissolution rate (dissolution rate at 5 minutes after the start of dissolution) is 60% or more, and the final dissolution rate (dissolution rate at 120 minutes after the start of dissolution) reaches 100%, whereas in all of the tablet of Comparative Example 1-1 in which the weight ratio of the lactose hydrate and microcrystalline cellulose is less than 1:1.5, the tablet of Comparative Example 1-2 in which the weight ratio of the lactose hydrate and microcrystalline cellulose is greater than 1:90, and the tablets of Comparative Examples 1-3 in which only microcrystalline cellulose is used as an excipient, the initial dissolution rate is less than 60%, indicating low initial dissolution properties. Moreover, it was confirmed that in the tablets of Comparative Examples 1-1 and 1-3, the main component is not completely dissolved out even after the lapse of 120 minutes, which is the final dissolution time point.

Accordingly, it can be confirmed that in the formulation for oral administration of the present disclosure containing the lactose hydrate and the microcrystalline cellulose in a weight ratio of 1:1.5 to 1:90 as a main ingredient and an excipient, the effect of improving the initial dissolution rate is exhibited at pH 1.2 and pH 4.0, which are the gastrointestinal environments of the living body, and the entire amount of the main component can be dissolved out before the final dissolution time.

Example 2-1

1-(5-(2,4-difluorophenyl)-1-((3-fluorophenyl) sulfonyl)-4-methoxy-1H-pyrrol-3-yl)-N-methylmethanamine hydrochloride (API) as the main component was mixed with microcrystalline cellulose, lactose hydrate and magnesium stearate. Then, the mixture was compressed by a roller compactor to prepare a plate-like compressed product, which was pulverized and granulated by an oscillator to prepare granules. Croscarmellose sodium as a disintegrant, yellow iron oxide as a colorant, and magnesium stearate as a lubricant were added to the prepared granules and mixed. The resulting mixture was compressed to prepare an uncoated tablet. A coating solution, which was prepared by dissolving/dispersing Opadry (Calacon) in purified water for 1 hour, was coated onto the prepared uncoated tablet, and then dried to prepare a coated tablet. The coating solution, which was prepared by dissolving/dispersing Opadry II (Calacon) in purified water and ethanol solution for 1 hour, was again coated onto the primary coated tablet to prepare a final tablet. At this time, the contents of the components contained in the tablet of Example 2-1 are as shown in Table 5 below.

Examples 2-2 to 2-3 and Reference Examples 2-1 to 2-3

A tablet was prepared in the same manner as in Example 2-1, except that the compounds described in Table 6 were used instead of croscarmellose sodium used as a disintegrant in Example 2-1.

TABLE 6

| | | (Amount used, part by weight) | | | | | |
|---|---|---|---|---|---|---|---|
| Category | Component | Example 2-1 | Reference Example 2-1 | Reference Example 2-2 | Example 2-2 | Example 2-3 | Reference Example 2-3 |
| Main component | API | 100 | 100 | 100 | 100 | 100 | 100 |

TABLE 6-continued

| Category | Component | Example 2-1 | Reference Example 2-1 | Reference Example 2-2 | Example 2-2 | Example 2-3 | Reference Example 2-3 |
|---|---|---|---|---|---|---|---|
| | | (Amount used, part by weight) | | | | | |
| Excipient | Microcrystalline cellulose | 199.8 | 199.8 | 199.8 | 199.8 | 199.8 | 199.8 |
| | Lactose hydrate | 52.5 | 52.5 | 52.5 | 52.5 | 52.5 | 52.5 |
| Disintegrant | Croscarmellose sodium | 15 | — | — | — | — | — |
| | Granulated powder mannitol | — | 15 | — | — | — | — |
| | Crospovidone | — | — | 15 | — | — | — |
| | Carboxymethylcellulose calcium | — | — | — | 15 | — | — |
| | Sodium starch glycolate | — | — | — | — | 15 | — |
| | Starch | — | — | — | — | — | 15 |
| Lubricant | Magnesium stearate | 7.5 | 7.5 | 7.5 | 7.5 | 7.5 | 7.5 |
| Colorant | Yellow iron oxide | 0.2 | 0.2 | 0.2 | 0.2 | 0.2 | 0.2 |
| Coating agent | Opadry | 7.5 | 7.5 | 7.5 | 7.5 | 7.5 | 7.5 |
| | Opadry II | 11.25 | 11.25 | 11.25 | 11.25 | 11.25 | 11.25 |
| Total amount | | 393.75 | 393.75 | 393.75 | 393.75 | 393.75 | 393.75 |
| Weight ratio of microcrystalline cellulose to lactose hydrate | | 3.81 | 3.81 | 3.81 | 3.81 | 3.81 | 3.81 |
| Main component content (wt. %) | | 25.4 | 25.4 | 25.4 | 25.4 | 25.4 | 25.4 |

Experimental Example 2: Storage Stability Test

The tablets prepared in Examples 2-1 to 2-3 and Reference Examples 2-1 to 2-3 were placed in a container (high-density polyethylene bottle, HDPE bottle), and then the tablets were stored for 4 or 8 weeks under accelerated conditions (40° C., 75% RH) while opening a cap, and an in vitro dissolution test and HPLC analysis were performed to measure the dissolution rate (%). The results are shown in Table 7 in comparison with the dissolution rate (initial) at the initial condition before storage. Further, the dissolution rates of the tablets prepared in Example 2-1, Reference Example 2-2, and Reference Example 2-3 under initial conditions and accelerated conditions are shown in FIGS. 3 to 5, respectively. At this time, the conditions of the dissolution test are as follows.

1) Basis for dissolution test: dissolution test of the general test method as set forth in the Korean Pharmacopoeia 11th edition
2) Dissolution test: dissolution test II, Paddle method
3) Dissolution test solution: 900 mL of pH 6.8 test solution
4) Temperature condition: maintained at 37.2° C.±0.5° C.
5) Analysis method: HPLC method
   Detector: ultraviolet absorbance spectrometer (measurement wavelength: 254 nm)
   Column: C8 5 um/4.6×250 mm column
   Mobile phase: hydrogen phosphate buffer: methanol
   pH 6.8 test solution: a second solution of the dissolution test according to the Korean Pharmacopoeia, which is a test solution prepared by mixing phosphate buffer and water in a 1:1 ratio

TABLE 7

| | Time (min) | 5 | 10 | 15 | 30 | 45 | 60 | 90 | 120 | 240 | 360 |
|---|---|---|---|---|---|---|---|---|---|---|---|
| Example 2-1 | Initial | 40.2 | 55.8 | 61.9 | 70.3 | 75.8 | 79.0 | 81.6 | 85.4 | 90.4 | 96.8 |
| | 4 weeks under acceleration | 36.2 | 46.7 | 55.2 | 64.9 | 71.4 | 77.0 | 81.8 | 86.1 | 93.7 | 97.2 |
| Reference Example 2-1 | Initial | 33.7 | 51.7 | 60.7 | 68.3 | 70.9 | 71.7 | 74.5 | 77.0 | 82.1 | 85.0 |
| | 4 weeks under acceleration | 29.0 | 46.8 | 53.4 | 59.9 | 62.9 | 65.4 | 68.9 | 71.8 | 78.5 | 83.0 |
| Reference Example 2-2 | Initial | 42.1 | 55.3 | 61.5 | 69.9 | 74.5 | 77.4 | 79.2 | 81.6 | 89.6 | 91.6 |
| | 4 weeks under acceleration | 32 | 43.7 | 50.3 | 58.2 | 62.3 | 65.9 | 70.1 | 73.5 | 81.1 | 87.6 |
| Example 2-2 | Initial | 38.1 | 54.2 | 60.4 | 67.3 | 71.9 | 72.6 | 75.6 | 77.9 | 83.6 | 87.7 |
| | 4 weeks under acceleration | 33.7 | 48.5 | 55.1 | 62.7 | 67.6 | 71.6 | 76.5 | 80.6 | 87.3 | 90.8 |
| Example 2-3 | Initial | 36.9 | 51.8 | 59 | 66.8 | 68.6 | 71 | 73.3 | 75.1 | 81.1 | 84.8 |
| | 4 weeks under acceleration | 31.6 | 47.9 | 57.3 | 63.4 | 66.2 | 69.5 | 72.6 | 76.4 | 81.0 | 84.1 |
| Reference Example 2-3 | Initial | 37.1 | 56.5 | 64.1 | 73.1 | 77.8 | 80.8 | 81.4 | 85.1 | 89.5 | 93.7 |
| | 4 weeks under acceleration | 32.7 | 46.5 | 54.1 | 63.0 | 67.3 | 70.1 | 72.5 | 77.0 | 83.5 | 88.4 |

Referring to Table 7 and FIGS. 3 to 5, it can be confirmed that the tablets of Examples 2-1, 2-2 and 2-3 using croscarmellose sodium, calcium carboxymethylcellulose and sodium starch glycolate respectively among various kinds of disintegrants, maintain the dissolution rate without decreasing dissolution rates under the accelerated conditions of the intestinal environment of the living body of pH 6.8, and exhibit excellent storage stability, as compared with the tablets of Reference Examples 2-1, 2-2 and 2-3 using granulated powder mannitol, crospovidone and starch, respectively.

Further, considering the dissolution rate data under the pH 6.8 condition of Experimental Example 2, it is confirmed that the tablets of Examples are partially released and absorbed in the in vivo stomach, and then the remaining tablets will exhibit a stable dissolution rate in the small intestine. Therefore, it can be expected that the formulation for oral administration containing the compound represented by Chemical Formula 1 or a pharmaceutically acceptable salt thereof exhibits high bioavailability in both the stomach and small intestine environments in vivo.

Further, the results of evaluating the content of the active ingredient (API) for the tablets of Example 2-1 and Reference Example 2-3 are shown in Table 8 below. At this time, the content evaluation was performed by the following method.

1) Content Test Method: About 10 g of a sample to be measured was taken, placed in a 500 mL volumetric flask, to which 225 mL of buffer solution was added, ultrasonically extracted for 30 minutes, completely dispersed, stirred for 30 minutes, and cooled to room temperature. Methanol was added thereto, then stirred for 30 minutes, cooled to room temperature, and then methanol was added to match the marked line. Next, an appropriate amount of this solution was taken and centrifuged, and then 25 mL of the supernatant was taken, placed in a 200 mL volumetric flask, to which the diluent was added to match the marked line. This solution was filtered through a 0.45 um membrane filter and used as the sample solution.
2) Buffer solution: a solution in which 1.74 g of dipotassium hydrogen phosphate was accurately weighted, 1000 ml of water was added and dissolved, and then add 1 mL of trifluoroacetic acid was added (pH 2.85±0.05).
3) Diluent: buffer solution: MeOH=45:55 (v/v)
4) Temperature condition: maintained at 37.2° C.±0.5° C.
5) Analysis method: HPLC method
   Detector: ultraviolet absorbance spectrometer (measurement wavelength: 254 nm)
   Column: C8 5 um/4.6×250 mm column
   Mobile phase: hydrogen phosphate buffer: methanol

TABLE 8

| Content (API) (%) | Example 2-1 | Reference Example 2-3 |
|---|---|---|
| Initial | 98.0 | 99.6 |
| 4 week-storage under accelerated condition | 98.0 | 98.2 |
| 8 week-storage under accelerated condition | 97.3 | 97.0 |

Referring to Table 8, it can be confirmed that the tablet of Example 2-1 using croscarmellose sodium as a disintegrant is not reduced in the content of the active ingredient even after long-term storage under accelerated conditions, as compared with the tablet of Reference Example 2-3 using starch.

Thereby, it is confirmed that the table which contains 1-(5-(2,4-difluorophenyl)-1-((3-fluorophenyl) sulfonyl)-4-methoxy-1H-pyrrol-3-yl)-N-methylmethanamine or a pharmaceutically acceptable salt thereof as an active ingredient and contains microcrystalline cellulose and lactose hydrate as excipients in a specific weight ratio exhibits excellent dissolution properties, sufficiently exhibits the intended drug effect while exhibiting an immediate effect, and thus can be suitably used as a pharmaceutical formulation.

Further, when the tablet additionally contains one of croscarmellose sodium, carboxymethylcellulose calcium and sodium starch glycolate as a disintegrant, excellent dissolution properties and active ingredient content are maintained even under accelerated conditions of the in vivo intestinal environment, thereby exhibiting more excellent storage stability.

Examples 3-1 to 3-3 and Reference Example 3-1

In order to evaluate the dissolution rate by particle size of the main component, 1-(5-(2,4-difluorophenyl)-1-((3-fluorophenyl) sulfonyl)-4-methoxy-1H-pyrrole-3-yl)-N-methylmethanamine hydrochloride, which is a compound represented by Chemical Formula 1 as a main component, was pulverized using a jet mill, and then of these, each main component having a particle size ($D_{50}$) of Table 9 was taken, and tablets of Examples 3-1 to 3-3 and Reference Example 3-1 were prepared in the same manner as in Example 2-1. The content of the components contained in each tablet is shown in Table 9 below. In addition, the particle size distribution ($D_{50}$) of the main component was measured as follows.

Particle size measurement (measured by volume average particle size by laser diffraction method)

1) Measuring instrument: Mastersizer 3000 from Malvern Instruments

2) Test solution 0.05% (v/v) Lecithin in hexane solution

3) Preparation of sample solution

About 10.0 mg of the sample was placed in a 20 ml beaker, 15 mL of the test solution was taken, which was subjected to ultrasonic treatments for 30 seconds, completely dispersed, and used as the sample solution.

4) Analysis method

The sample solution was added so that the obscuration level became 5% to 10%, confirmed that the obscuration level was stabilized, and then the measurement was performed according to the following conditions.

[Operation Conditions]

Range: 0.02~2000 μm

Particle RI: 1.59

Absorption: 0.01

Dispersant RI: 1.380

Obscuration Range: 5~10%

Stirrer/Pump speed: 3000 RPM

Ultrasonic sound: off

Measurement cycle: 5

TABLE 9

| Category | Component | (Amount used, part by weight) Example 3-1 | Example 3-2 | Example 3-3 | Reference Example 3-1 |
|---|---|---|---|---|---|
| Main component | API | 100 | 100 | 100 | 100 |
| Excipient | Microcrystalline cellulose | 199.8 | 199.8 | 199.8 | 200 |
| | Lactose hydrate | 52.5 | 52.5 | 52.5 | 52.5 |
| Disintegrant | Croscarmellose sodium | 15 | 15 | 15 | 15 |
| Lubricant | Magnesium stearate | 7.5 | 7.5 | 7.5 | 7.5 |
| Colorant | Yellow iron oxide | 0.2 | 0.2 | 0.2 | 0.2 |
| Coating agent | Opadry | 7.5 | 7.5 | 7.5 | 7.5 |
| | Opadry II | 11.25 | 11.25 | 11.25 | 7.5 |
| Total amount | | 393.75 | 393.75 | 393.75 | 390.2 |
| Weight ratio of microcrystalline cellulose to lactose hydrate | | 3.81 | 3.81 | 3.81 | 3.81 |
| Main component content (wt. %) | | 25.4 | 25.4 | 25.4 | 25.6 |
| Main component particle size ($D_{50}$, μm) | | 16 | 18 | 65 | 115 |

Experimental Example 3: Dissolution Evaluation Test by Particle Size

The tablets prepared in Examples 3-1 to 3-2 and Reference Examples 3-1 to 3-2 were subjected to an in vitro dissolution test and a HPLC analysis with the pH 1.2 test solution, and the dissolution rate (%) was measured. The results are shown in Table 10 and FIG. 6. At this time, the conditions of the dissolution test are as follows.

1) Basis for dissolution test: dissolution test of the general test method as set forth the Korean Pharmacopoeia 11th edition
2) Dissolution test: dissolution test II, Paddle method
3) Dissolution test solution: 900 mL of pH 1.2 test solution
4) Temperature condition: maintained at 37.2° C.±0.5° C.
5) Analysis method: HPLC method
   Detector: ultraviolet absorbance spectrometer (measurement wavelength: 254 nm)
   Column: C8 5 um/4.6×250 mm column
   Mobile phase: hydrogen phosphate buffer: methanol
   pH 1.2 test solution: a first solution of the dissolution test according to the Korean Pharmacopoeia, which is a buffer solution prepared by using hydrochloric acid and sodium chloride having a hydrochloric acid concentration of 0.1 mol/L.

TABLE 10

| Time (min) | 5 | 10 | 15 | 30 | 45 | 60 | 90 | 120 |
|---|---|---|---|---|---|---|---|---|
| Example 3-1 | 64.6 | 75.9 | 80.5 | 84.0 | 87.4 | 89.4 | 92.1 | 93.9 |
| Example 3-2 | 64.1 | 72.8 | 75.6 | 79.5 | 82.0 | 84.1 | 87.1 | 89.4 |
| Example 3-3 | 60.1 | 73.5 | 77.4 | 84.4 | 87.3 | 89.1 | 93.0 | 96.2 |
| Reference Example 3-1 | 37.8 | 47.3 | 53.5 | 57.1 | NA | 63.8 | NA | 70.3 |

Referring to Table 10 and FIG. 6, it can be confirmed that in the tablets of Examples 3-1 to 3-3, the initial dissolution rate (dissolution rate at 5 minutes after the start of dissolution) is 60% or more under pH 1.2 conditions, the final dissolution rate (dissolution rate at 120 minutes after the start of dissolution) is 89% or more, and the overall dissolution pattern is similar, whereas the tablet of Reference Example 3-1 is low in the final dissolution rate as well as in the initial dissolution rate, as compared with those of Examples. In addition, the tablets of Examples 3-2 and 3-3 have the similarity factor ($f_2$) value of 50% or more, which is equivalent to the tablets of Example 3-1, as measured according to the pharmaceutical equivalence test standard, whereas the tablet of Reference Example 3-1 has the similarity factor ($f_2$) value of less than 50%, which showed a significant difference from those of Example 3-1 as measured according to the pharmaceutical equivalence test standard. As a result, it can be confirmed that the particle size of the main component affects the dissolution profile of the final formulation, and when the particle size ($D_{50}$) of the main component is 100 μm or less, it is judged that the uniform quality of the formulation and the efficacy in the body can be ensured.

The invention claimed is:

1. A formulation for oral administration comprising:

1) A compound represented by the following Chemical Formula 1 or a pharmaceutically acceptable salt thereof; and
2) An excipient comprising lactose hydrate and microcrystalline cellulose, wherein the lactose hydrate and the microcrystalline cellulose are contained in a weight ratio of lactose hydrate to microcrystalline cellulose of 1:3.2 to 1:60:

[Chemical Formula 1]

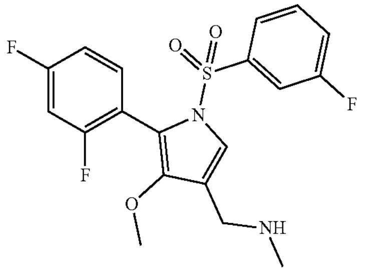

wherein the formulation for oral administration further comprises a disintegrant, and wherein the disintegrant is at least one selected from the group consisting of croscarmellose sodium, carboxymethylcellulose calcium and sodium starch glycolate.

2. The formulation for oral administration according to claim 1, wherein the lactose hydrate and the microcrystalline cellulose are contained in a weight ratio of lactose hydrate to microcrystalline cellulose of 1:3.4 to 1:5.0.

3. The formulation for oral administration according to claim 1, wherein the excipient is contained in an amount of 100 parts by weight to 1400 parts by weight based on 100 parts by weight of the compound represented by Chemical Formula 1 or a pharmaceutically acceptable salt thereof.

4. The formulation for oral administration according to claim 1, wherein the excipient is contained in an amount of 200 parts by weight to 650 parts by weight based on 100 parts by weight of the compound represented by Chemical Formula 1 or a pharmaceutically acceptable salt thereof.

5. The formulation for oral administration according to claim 1, wherein the lactose hydrate is contained in an amount of 1 parts by weight to 350 parts by weight based on 100 parts by weight of the compound represented by Chemical Formula 1 or a pharmaceutically acceptable salt thereof.

6. The formulation for oral administration according to claim 1, wherein the microcrystalline cellulose is contained in an amount of 50 parts by weight to 1100 parts by weight based on 100 parts by weight of the compound represented by Chemical Formula 1 or a pharmaceutically acceptable salt thereof.

7. The formulation for oral administration according to claim 1, wherein the disintegrant is croscarmellose sodium.

8. The formulation for oral administration according to claim 1, wherein the disintegrant is contained in an amount of 3.5 parts by weight to 80 parts by weight based on 100 parts by weight of the compound represented by Chemical Formula 1 or a pharmaceutically acceptable salt thereof.

9. The formulation for oral administration according to claim 1, wherein the formulation for oral administration further comprises at least one additive selected from the group consisting of a binder, a lubricant, a colorant, and a coating agent.

10. The formulation for oral administration according to claim 1, wherein the formulation for oral administration further comprises magnesium stearate and yellow iron oxide.

11. The formulation for oral administration according to claim 1, wherein the compound represented by Chemical Formula 1 or a pharmaceutically acceptable salt thereof is contained in an amount of 5% by weight to 50% by weight based on the total weight of the formulation for oral administration.

12. The formulation for oral administration according to claim 1, wherein the compound represented by Chemical Formula 1 or a pharmaceutically acceptable salt thereof is contained in an amount of 10% by weight to 30% by weight based on the total weight of the formulation for oral administration.

13. The formulation for oral administration according to claim 1, wherein the compound represented by Chemical Formula 1 or a pharmaceutically acceptable salt thereof has a particle size ($D_{50}$) of 100 μm or less.

14. The formulation for oral administration according to claim 1, wherein the formulation for oral administration has a total weight of 80 mg to 350 mg.

15. The formulation for oral administration according to claim 1, wherein the compound represented by Chemical Formula 1 or a pharmaceutically acceptable salt thereof is contained in an amount of 10 mg to 80 mg per one formulation.

* * * * *